United States Patent
Li et al.

(10) Patent No.: US 12,303,576 B2
(45) Date of Patent: *May 20, 2025

(54) TWO PHASE WATER-BASED SMUDGE-RESISTANT MAKE-UP REMOVER

(71) Applicant: L'OREAL, Paris (FR)

(72) Inventors: Zhi Li, Philadelphia, PA (US); Hy Si Bui, Piscataway, NJ (US)

(73) Assignee: L'OREAL, Paris (FR)

(*) Notice: Subject to any disclaimer, the term of this patent is extended or adjusted under 35 U.S.C. 154(b) by 0 days.

This patent is subject to a terminal disclaimer.

(21) Appl. No.: 17/217,742

(22) Filed: Mar. 30, 2021

(65) Prior Publication Data
US 2022/0313568 A1 Oct. 6, 2022

(51) Int. Cl.
| | | |
|---|---|---|
| *A61K 8/03* | (2006.01) | |
| *A61K 8/31* | (2006.01) | |
| *A61K 8/44* | (2006.01) | |
| *A61Q 1/14* | (2006.01) | |
| *A61Q 19/10* | (2006.01) | |

(52) U.S. Cl.
CPC .............. *A61K 8/03* (2013.01); *A61Q 1/14* (2013.01); *A61Q 19/10* (2013.01); *A61K 8/31* (2013.01); *A61K 8/44* (2013.01)

(58) Field of Classification Search
None
See application file for complete search history.

(56) References Cited

U.S. PATENT DOCUMENTS

| | | | | |
|---|---|---|---|---|
| 2002/0031478 A1* | 3/2002 | Keller | ............... | A61K 8/891 424/70.27 |
| 2004/0081674 A1* | 4/2004 | Franke | ............... | A61K 8/33 424/401 |
| 2011/0124543 A1* | 5/2011 | Lutrario | ............... | A61K 8/345 510/126 |
| 2016/0367959 A1 | 12/2016 | Lapriore et al. | | |
| 2022/0023160 A1* | 1/2022 | Kariya | ............... | A61Q 1/14 |

FOREIGN PATENT DOCUMENTS

| | | |
|---|---|---|
| EP | 1593364 B1 | 10/2008 |
| JP | 2004196713 A | 7/2004 |
| JP | 2018162222 A | 10/2018 |
| JP | 2020050640 A | 4/2020 |
| KR | 20090004048 A | 1/2009 |
| KR | 20090004050 A | 1/2009 |
| WO | 2014018543 A1 | 1/2014 |

OTHER PUBLICATIONS

Knowde "Ajinomoto CAE" <https://www.knowde.com/stores/ajinomoto/products/ajinomoto-cae> available Nov. 15, 2020; accessed Mar. 19, 2024 (Year: 2020).*

Suzuki et al. "A family of low-molecular-weight organogelators based on Na, N3-diacyl-L-lysine: effect of alkyl chains on their organogelation behavior", Tetrahedron, vol. 64, 2008, p. 10395-10400, Elsevier.

Search Report issued to French counterpart Application No. 2107608 dated Mar. 24, 2022.

PCT Notification of Transmittal of the International Search Report and the Written Opinion of the International Searching Authority, or the Declaration issued to counterpart Application No. PCT/IB2022/052962 dated Jun. 29, 2022.

* cited by examiner

*Primary Examiner* — Nicole P Babson
(74) *Attorney, Agent, or Firm* — McNees Wallace & Nurick LLC

(57) ABSTRACT

A cleansing composition includes at least two visually distinct phase layers that include a first visually distinct phase layer including at least one amino-acid derived cationic surfactant, and at least one inorganic salt, and a second visually distinct phase layer including at least one plant-derived alkane or plant-derived alkylether. The at least one cationic surfactant is an amino acid based cationic surfactant that may be selected from a derivative ethyl lauroyl arginate or a salt thereof, and ethyl cocoyl arginate or a salt thereof (PCA ethyl cocoyl arginate). The first visually distinct phase layer may be present at about 50% to about 95% and the second visually distinct phase layer may be present at about 5% to about 50%, by weight, based on the total weight of the cleansing composition.

20 Claims, No Drawings

TWO PHASE WATER-BASED SMUDGE-RESISTANT MAKE-UP REMOVER

FIELD

This invention relates to a nature-based make-up removal and cleansing composition provided in a multi-phase formula that includes two visually distinct phases and provides visually and tactically desirable properties with natural ingredients and which provides effective cleansing and makeup removal.

BACKGROUND

Multiphase liquid cleansing compositions provide excellent aesthetic appearance and are very attractive for consumers and have been proposed for uses related to bath/shower, makeup removals, and hair. When left standing, a multi-phase liquid forms two or more visibly distinct phases. When agitated, the cleansing composition forms a visible single phase, which separates and returns to the multiple visibly distinct phases. Often such compositions include one or more of emulsifying surfactants and polymers, and volatile silicone oils and other similar synthetic compositions, any or all of which can be irritating to skin or eyes.

Consumers who seek cosmetic products that are less irritating, and that are formed on the basis of natural constituents, may seek to avoid cosmetics that include such harsh ingredients. Further, consumers increasingly desire cosmetic products with high sustainability profiles, positive environment impacts, and compliances to common principles of social responsibility. As a result, cleansing compositions made of chemicals derived from non-animal, non-petrochemical, and renewable sources are greatly preferred. To help consumers understand a product's sustainability profile, industrial standards like ISO 16128 were developed to allow percentages of natural origin of the product formula to be properly calculated and labelled on the packaging. Great efforts have been made to develop "highly natural" or "all natural" cosmetic products, in which over 99% or all carbon atoms from intentionally added ingredients are from natural sources.

There are several examples in the art of multi-phase cleansing compositions with desirable aesthetics. For example, US20160367959 provides a three-phase cosmetics composition in which one of the liquids comprises a triglyceride oil, another comprises a silicone oil, and a third liquid comprises a polyalkylene glycol. In another example, EP 1593364 provides a three-phase cosmetics composition for keratin fibers especially for hair that includes an oily first phase, a second phase that contains an ethoxylated glyceryl fatty acid monoester, and a third phase that includes polyols. And in another example, WO 2014018543 provides a three-phase cosmetics composition for treating hair that includes an oil phase, a polyol phase, and a silicone phase. Further, in another example, KR20090004048 provides a three-phase cosmetics composition in which the bottom layer includes 1 to 10 parts by weight of water and 15 to 30 parts by weight of palm oil fatty acid polyoxyethylene glycerin, a middle layer includes 15 to 40 parts by weight of glycerin, and an upper layer includes 20 to 50 parts by weight of mineral oil. Further, in another example, KR20090004050 provides a four-phase cosmetics composition for cleansing in which the bottom layer includes 5-10 weight part of water and 15-30 weight part of palm oil fatty acid polyoxyethylene glycerol, the lower middle layer includes 10 to 20 parts by weight of glycerin, the upper middle layer includes 15 to 25 parts by weight of dimethicone, and the upper layer includes 10 to 30 parts by weight of mineral oil. These various compositions provide some of the desired aesthetic benefits sought by consumers relating to the visual and tactile feel of multi-phase compositions, but none of them is "highly natural" or "natural."

It remains technically challenging for a multi-phase liquid cleansing composition to achieve satisfactory phase separation performances and high natural content. Accordingly, there is a need for a cleansing composition, in particular a make-up removing cleanser, that is "highly natural" or "all natural" in a multi-phase liquid form that is aesthetic appealing and has good phase separation performance.

The instant invention overcomes the disadvantages of the art as pertains to make-up removing compositions that include ingredients that are primarily natural or nature-based in an aesthetically pleasing multi-phase formulation with a sharp phase interfaces and which allows easy make-up removal that is comparable to or improved over prior art compositions, and is not greasy, and includes little or no components that may be irritating to the skin or eyes.

SUMMARY

The disclosure provides, in various embodiments, a cleansing composition including: at least two visually distinct phase layers that include a first visually distinct phase layer including at least one amino-acid derived cationic surfactant, and at least one inorganic salt, and a second visually distinct phase layer including at least one plant-derived alkane or plant-derived alkylether.

In some embodiments, the at least one cationic surfactant is selected from the group consisting of an amino acid based cationic surfactant selected from the group consisting of a derivative ethyl lauroyl arginate or a salt thereof, and ethyl cocoyl arginate or a salt thereof (PCA ethyl cocoyl arginate).

In some embodiments, the at least one inorganic salt is selected from the group consisting of sea salt, sodium chloride, magnesium chloride, calcium chloride, potassium chloride, magnesium sulfate, magnesium carbonate, calcium carbonate, and zinc pyrrolidone carboxylic acid, and other suitable mineral salts of sodium, calcium, magnesium, potassium, zinc, and combinations thereof.

In some embodiments, the at least one plant-derived alkane or plant-derived alkylether in the second visually distinct phase layer includes an alkylether selected from the group consisting of dicaprylyl ether, dicapryl ether, dilauryl ether, diisostearyl ether, dioctyl ether, nonyl phenyl ether, dodecyl dimethylbutyl ether, cetyl dimethylbutyl ether, cetyl isobutyl ether, and combinations thereof.

In some embodiments, the first visually distinct phase layer includes the at least one cationic surfactant present in the cleansing composition from about 0.03% to about 1%, by weight, based on the total weight of the cleansing composition.

In some embodiments, the first visually distinct phase layer includes the at least one inorganic salt present in the cleansing composition from about 0.1% to about 2%, by weight, based on the total weight of the cleansing composition.

In some embodiments, the first visually distinct phase layer is present in the cleansing composition at about 50% to about 95%, by weight, based on the total weight of the cleansing composition, and wherein the second visually distinct phase layer is present in the cleansing composition at about 5% to about 50%, by weight, based on the total weight of the cleansing composition.

In some embodiments, the cleansing composition, when agitated, forms a milky single phase which separates after agitation into three or more visibly distinct phases in a maximum period of 24 hours, and wherein the cleansing composition demonstrates essentially no clinging or dragging of a layer on a container wall and there are no or minimal liquid droplets visible at any phase interface.

In some embodiments, the composition further includes at least one nonionic surfactant selected from the group consisting of lauryl glucoside, octyl glucoside, decyl glucoside, coco glucoside, caprylyl/capryl glucoside, sodium lauryl glucose carboxylate, and combinations thereof.

In some embodiments, the first visually distinct phase layer includes at least one cosmetically acceptable solvent selected from the group consisting of water, water based solvents, and combinations thereof.

In some embodiments, the first visually distinct phase layer includes at least one cosmetically acceptable solvent including water, and one or more of glycerin or propanediol.

In some embodiments, the cleansing composition includes at least a top and a bottom layer, and wherein the visually distinct phase layer including at least one plant-derived alkane or plant-derived alkylether is the top layer, and the visually distinct phase layer including at least one amino-acid derived cationic surfactant and at least one inorganic salt is the bottom layer.

In some embodiments, the cleansing composition includes one or more additional phase layers.

In some embodiments, the cleansing composition includes one or more additional phase layers, wherein any one or more of the additional phase layers is selected from the group consisting of (i) a visually distinct phase layer including at least one cosmetic solvent having a Hildebrand solubility parameter δ value that is greater than 15 $cal^{1/2}$ $cm^{-3/2}$ and including at least one cationic surfactant and at least one inorganic salt; (ii) a visually distinct phase layer including at least one cosmetic solvent having a Hildebrand solubility parameter δ value less than 7.5 $cal^{1/2}$ $cm^{-3/2}$; (iii) a visually distinct phase layer including at least one cosmetic solvent having a Hildebrand solubility parameter δ value that is between 8 and 10 $cal^{1/2}$ $cm^{-3/2}$; or combinations thereof.

In some embodiments, the cleansing composition includes an additional visually distinct phase layer including at least one cosmetic solvent having a Hildebrand solubility parameter δ value that is less than 7.5 $cal^{1/2}$ $cm^{-3/2}$ or that is between 8 and 10 $cal^{1/2}$ $cm^{-3/2}$.

In some embodiments, the cleansing composition includes an additional visually distinct phase layer including isododecane.

The disclosure provides, in some embodiments, a cleansing composition including: at least two visually distinct phase layers that include (a) a first visually distinct phase layer including at least one amino-acid derived cationic surfactant selected from the group consisting of an amino acid based cationic surfactant selected from the group consisting of a derivative ethyl lauroyl arginate or a salt thereof, and ethyl cocoyl arginate or a salt thereof (PCA ethyl cocoyl arginate), and at least one inorganic salt selected from the group consisting of sea salt, sodium chloride, magnesium chloride, calcium chloride, potassium chloride, magnesium sulfate, magnesium carbonate, calcium carbonate, and zinc pyrrolidone carboxylic acid, and other suitable mineral salts of sodium, calcium, magnesium, potassium, zinc, and combinations thereof, and at least one nonionic surfactant selected from the group consisting of lauryl glucoside, octyl glucoside, decyl glucoside, coco glucoside, caprylyl/capryl glucoside, sodium lauryl glucose carboxylate, and combinations thereof, and (b) a second visually distinct phase layer including at least one plant-derived alkylether selected from the group consisting of dicaprylyl ether, dicapryl ether, dilauryl ether, diisostearyl ether, dioctyl ether, nonyl phenyl ether, dodecyl dimethylbutyl ether, cetyl dimethylbutyl ether, cetyl isobutyl ether, and combinations thereof.

In some embodiments, the first visually distinct phase layer includes the at least one cationic surfactant present in the cleansing composition from about 0.03% to about 1% and includes the at least one inorganic salt present in the cleansing composition from about 0.1% to about 2%, and wherein the second visually distinct phase layer includes at least one plant-derived alkylether present in the cleansing composition at about 5% to about 50%, all amounts by weight, based on the total weight of the cleansing composition.

The disclosure also provides, in various embodiments, a method for forming a multi-phase cleansing composition, the method including: forming (a) a first phase layer including at (i) least one amino-acid derived cationic surfactant or (ii) at last one amino-acid derived cationic surfactant and at least one nonionic surfactant, and at least one inorganic salt; (b) forming a second phase layer including at least one plant-derived alkane or alkylether; combining the first and second phase layers to provide a multi-phase cleansing composition wherein each of the phase layers are visually distinct, and wherein, when agitated, the cleansing composition forms a milky single phase which separates after agitation into two or more visibly distinct phases in a maximum period of 24 hours.

In some embodiments of the method for forming a multi-phase cleansing composition:
  in the first phase layer, the at least one cationic surfactant is an amino acid based cationic surfactant selected from the group consisting of a derivative ethyl lauroyl arginate or a salt thereof, and ethyl cocoyl arginate or a salt thereof (PCA ethyl cocoyl arginate), the at least on nonionic surfactant, if present, is selected from the group consisting of lauryl glucoside, octyl glucoside, decyl glucoside, coco glucoside, caprylyl/capryl glucoside, sodium lauryl glucose carboxylate, and combinations thereof; the at least one inorganic salt selected from the group consisting of sea salt, sodium chloride, magnesium chloride, calcium chloride, potassium chloride, magnesium sulfate, magnesium carbonate, calcium carbonate, and zinc pyrrolidone carboxylic acid, and other suitable mineral salts of sodium, calcium, magnesium, potassium, zinc, and combinations thereof;
  in the second phase layer, the at least one plant-derived alkane or alkylether includes at least an alkylether selected from the group consisting of dicaprylyl ether, dicapryl ether, dilauryl ether, diisostearyl ether, dioctyl ether, nonyl phenyl ether, dodecyl dimethylbutyl ether, cetyl dimethylbutyl ether, cetyl isobutyl ether, and combinations thereof. In some embodiments, the cleansing composition includes at least a top and a bottom layer, and In some embodiments, the first phase layer is the bottom layer, the second phase layer is the top layer.

In some embodiments, the inventive cleansing composition demonstrates phase separation after shaking. In some embodiments, when agitated, the cleansing composition forms a milky single phase which separates after agitation into three or more visibly distinct phases in a maximum period of 24 hours. In some embodiments, the inventive cleansing composition demonstrates phase separation after shaking wherein after agitation is ceased, demonstrates slow initial phase separation to enable sufficient homogenous emulsion before dispensing. In some embodiments, the inventive cleansing composition demonstrates after agitation is ceased and there is a clear container wall with minimal liquid droplet visible to the eye wherein there are essentially no clinging or dragging of a layer on a container wall and there are no or minimal liquid droplets visible at any phase interface. In some embodiments, the cleansing composition demonstrates excellent ability to remove both long wear mascara and long wear foundation.

In accordance with some embodiments of the cleansing composition, the at least one cosmetically acceptable solvent with a Hildebrand solubility parameter δ value greater than 15 $cal^{1/2}$ $cm^{-3/2}$ may be selected from water and water based solvents, nonionic surfactants, and the like.

In accordance with some embodiments of the cleansing composition, the at least one cosmetically acceptable solvent with a Hildebrand solubility parameter δ value less than 7.5 $cal^{1/2}$ $cm^{-3/2}$ may be selected from oil and oil based solvents, and the like.

In accordance with some embodiments of the cleansing composition, the at least one cosmetically acceptable solvent with a Hildebrand solubility parameter δ value between 8 and 10 $cal^{1/2}$ $cm^{-3/2}$ may be selected from oil and oil based solvents, plasticizers, alcohol, and the like.

In accordance with some embodiments, the cleansing composition also comprises one or more additional components selected from:

i. one or more humectants.
ii. one or more preservatives;
iii. one or more cosmetically acceptable additives;
iv. and combinations thereof.

In various embodiments, the cleansing composition may further include one or more cosmetically acceptable additives selected from fragrances; colorants; essential oils; fruit extracts, for example *Pyrus Malus* (Apple) Fruit Extract, and *Aloe Barbadensis* Leaf Juice Powder; citric acid, sodium chloride; neutralizing or pH-adjusting agents (e.g., triethylamine (TEA) and sodium hydroxide); and combinations thereof.

In some particular embodiments, the cleansing composition lacks, or is free or essentially free of silicones, in particular volatile silicones, for example but not limited to, cyclomethicones such as cyclopentasiloxane, surfactants, parabens, formaldehyde, and formaldehyde-derived compounds. In some embodiments, the cleansing composition lacks, or is free or essentially free of any one or a combination of silicone oils, isoparaffins, mineral oils, polyethylene glycol (PEG), polypropylene glycol (PPG) surfactants or solvents, petrochemical-derived compounds like benzalkonium chloride, preservatives such as phenoxyethanol, or combinations thereof.

These and other aspects of the invention are set out in the appended claims and described in greater detail in the detailed description of the invention.

This disclosure describes exemplary embodiments in accordance with the general inventive concepts and is not intended to limit the scope of the invention in any way. Indeed, the invention as described in the specification is broader than and unlimited by the exemplary embodiments set forth herein, and the terms used herein have their full ordinary meaning.

It is to be understood that both the foregoing general description and the following detailed description are exemplary and explanatory only and are not restrictive of the disclosure.

DETAILED DESCRIPTION

In various embodiments, the disclosure provides a cleansing composition for make-up removal that provides an aesthetically pleasing gliding application and is smudge resistant. In an exemplary embodiment, an inventive make-up removal composition according to the disclosure is in the form of a water-based micellar make-up removal composition comprising at least two surfactants, one or more powdered polysaccharides, and water. The cleansing composition can also include one or more inorganic mineral powders, one or more humectants, one or more silicone-based defoaming agents, one or more preservatives, and other cosmetically acceptable additives.

The inventors hereof have surprisingly demonstrated with the cleansing composition that a nature-based formulation that lacks harsh surfactants, silicones, and thickeners unexpectedly provides appealing aesthetics when applied to skin and exhibits good multiphase properties. The cleansing composition includes at least three or more visually distinct liquid phases (phase layers). At least one of the at least three visually distinct phase layers includes at least one cationic surfactant and at least one inorganic salt, such phase layer present in an amount, by weight of the cleansing composition in a range from about 20% to about 80% and has at least one cosmetically acceptable solvent with a Hildebrand solubility parameter δ value greater than 15 $cal^{1/2}$ $cm^{-3/2}$. At least one of the at least three visually distinct phase layers includes at least one cationic surfactant and at least one inorganic salt, such phase layer present in an amount, by weight of the cleansing composition in a range from about 5% to about 50% and has at least one cosmetically acceptable solvent with a Hildebrand solubility parameter δ value less than 7.5 $cal^{1/2}$ $cm^{-3/2}$. And at least one of the at least three visually distinct phase layers is present in an amount, by weight of the cleansing composition in a range from about 5% to about 50% and has at least one cosmetically acceptable solvent with a Hildebrand solubility parameter δ value between 8 and 10 $cal^{1/2}$ $cm^{-3/2}$. When agitated, the cleansing composition forms a milky single phase, which separates after agitation into three or more visibly distinct phases in a maximum period of 24 hours.

"All Natural" as used herein means that all carbon atoms of intentionally added ingredients are from natural sources per ISO 16128.

"Cleanser" or "cleansing composition" as used herein means and refers to any cleansing composition utilized for application to a keratinous tissue for one or more of cleansing the skin, removal of make-up and the like.

"Cosmetically acceptable" as used herein means and refers to a carrier that is compatible with any keratinous substrate.

"Keratinous substrate" and "keratinous tissue" as used herein means and refers to, but is not limited to, skin, hair, and nails.

"Multi-phase" as used herein means and refers to compositions that include two, three, four or more phases which are separated by a single-phase interface. In accordance with the instant disclosure, the cleansing composition includes at least three such phases. A multiphase composition requires shaking prior to application in order to form an extemporaneous emulsion of the multiple phases, wherein after shaking has ceased the phases become rapidly being to separate and wherein within a period of time after shaking that can range from a few seconds to a few hours the phases become essentially completely separated and regain their initial state with distinct phase interfaces. The phenomenon of rapid phase separation, or de-mixing, of the phases after their use is one of the desired aesthetic qualities of multi-phase compositions The inventive composition achieves this property with high natural ingredient content and with no or with minimal synthetic components such as synthetic oils, for example, silicone oils, such as cyclopentasiloxane, and without thickeners.

"Natural or "Nature-based" as used herein means and refers to cosmetically acceptable materials and components that are one or more of directly obtained from nature, are obtained from nature with minimal processing, and are derivatives of materials that are obtained from nature. Cleansing composition according to the instant disclosure are in some embodiments up to 99.11% natural, or "Highly natural."

"Plant-derived oils" as used herein means fatty plant-derived oils that contain one or more fatty chain, and in some embodiments the fatty chain has a chain length from and including C8 to C24. Thus, in some embodiments, a fatty plant-derived oil may comprise one or a blend of oils having a chain length of C8, C9, C10, C11, C12, C13, C14, C15, C16, C17, C18, C19, C20, C21, C22, C23, and C24.

"Free" and "devoid" each indicates that no reliably measurable excluded material, for example, an excluded volatile silicone oil or excluded surfactant or other excluded material as described herein, is present in the cleansing composition. The term "essentially free" means that, while it is preferred that no excluded material is present in the cleansing composition, it is possible to have very small amounts of the excluded material in the cleansing composition of the invention, provided that these amounts do not materially affect the advantageous properties of the cleansing composition. In particular, "essentially free" means that excluded material can be present in the cleansing composition at an amount of less than 5%, or less than 4%, or less than 3%, or less than 2%, or less than 1%, or less than 0.1% by weight, based on the total weight of the cleansing composition.

"Silicone-free" means that excluded silicones have not been added as a component. In some embodiments, a composition is devoid of silicones. Some specific but non-limiting examples of silicones that are lacking from the cosmetic cleansing composition includes, but is not limited to, silicone polymers, for example selected from dimethicone, cyclopentasiloxane, and other silicone oils, and silicone elastomers.

"Petrochemical-free" means that excluded petrochemical have not been added as a component. Some specific but non-limiting examples of petrochemicals that are lacking from the cosmetic cleansing composition include benzalkonium chloride, isododecane, isohexadecane and the like. In some embodiments, the cleansing composition is not free from petrochemicals, but is formulated to have an amount of petrochemicals that is at or below the amounts found in similar compositions that are commercially available.

"Surfactant-free" means that excluded surfactants have not been added as a component. In some particular embodiments, the cleansing composition is devoid of surfactants. In some embodiments, the cleansing composition is devoid of ethylene glycol (PEG) based surfactants or of sulfate/sulfonate based surfactant, or combinations thereof. Those of skill in the art will appreciate that a surfactant may be present in a composition via its presence in one or more of the formulation components; thus, in some embodiments the cleansing composition may be "essentially surfactant-free" wherein surfactant is present at a concentration that does not exceed 5% by weight, and in some instances is present not more than 3% by weight, and in some instances is present not more than 1% by weight, based on the weight of the cosmetic cleansing composition. In some particular embodiments "surfactant-free" means that the cosmetic cleansing composition is free or devoid specifically of surfactant. Some specific but non-limiting examples of surfactants that are lacking from the cleansing composition includes those with a C10-C20 fatty alcohol or acid hydrophobe condensed with from about 2 to about 100 moles of ethylene oxide or propylene oxide per mole of hydrophobe; C2-C10 alkyl phenols condensed with from 2 to 20 moles of alkylene oxide; mono- and di-fatty acid esters of ethylene glycol; fatty acid monoglyceride; sorbitan; mono- and di-C8-C20 fatty acids; polyoxyethylene sorbitan; alkyl polyglycosides and saccharide fatty amides (e.g. methyl gluconamides); alkyl ether sulfate and sulfonates; alkyl sulfates and sulfonates; alkylbenzene sulfonates; alkyl and dialkyl sulfosuccinates; C8-C20 acyl isethionates; C8-C20 alkyl ether phosphates; alkylethercarboxylate. Some specific surfactants that are lacking from the cosmetic cleansing composition include PEG-100 Stearate; PEG-20 Stearate and other esters of Poly(Ethylene Glycol); Sucrose Stearate and other emulsifiers based on sugar esters; Glyceryl Stearate and other glycerol esters; Disodium Ethylene Dicocamide PEG-15 Disulfate; Sodium Steroyl Glutamate and other fatty amides; Steareth-100 and other fatty ethers; Acrylates/C10-30 Alkyl Acrylate Crosspolymer and similar polymeric emulsifiers.

"Skin" as used herein means and refers to skin materials containing keratin such as facial and body skin, scalp, eyebrows, and lips.

The definition and determination of Hildebrand solubility parameter for a liquid were previously disclosed by C. D. Hildebrand in his article titled "Using Solubility Parameters in Cosmetics Formulation" J. Soc. Cosmet. Chem., 36, 319-333 (September/October 1985).

Phases of the Multi-Phase Composition

The cleansing composition includes at least two or more visually distinct liquid phases (phase layers). In some embodiments, the cleansing composition includes two visually distinct phase layers. In some embodiments, the cleansing composition includes more than two visually distinct phase layers, for example four or more.

The cleansing composition includes at least two visually distinct phase layers that include a first visually distinct phase layer including at least one amino-acid derived cationic surfactant, and at least one inorganic salt, and a second visually distinct phase layer including at least one plant-derived alkane or plant-derived alkylether. The at least one cationic surfactant is an amino acid based cationic surfactant that may be selected from a derivative ethyl lauroyl arginate or a salt thereof, and ethyl cocoyl arginate or a salt thereof (PCA ethyl cocoyl arginate). The first visually distinct phase layer may be present at about 50% to about 95% and the second visually distinct phase layer may be present at about 5% to about 50%, by weight, based on the total weight of the cleansing composition.

When agitated, the cleansing composition forms a milky single phase, which separates after agitation into three or more visibly distinct phases in a maximum period of 24 hours.

Amino Acid Derived Cationic Surfactant

In the various embodiments, the cleansing composition includes at least one cationic surfactant.

In some representative embodiments, the cationic surfactant is an amino acid based cationic surfactant, and in some particular embodiments, the amino acid based cationic surfactant is selected from the group consisting of a derivative ethyl lauroyl arginate or a salt thereof, and ethyl cocoyl arginate or a salt thereof (PCA ethyl cocoyl arginate). In some other examples, the amino acid based cationic surfactant is selected from the group consisting of cationic lysine-based surfactants. Examples of amino acid-based cationic surfactants can be found in the literature like Tripathy, Divya, Mishra, Anuradha, Clark, James Hanley orcid.org/0000-0002-5860-et al (2018) Synthesis, chemistry, physico-chemical properties and industrial applications of amino acid surfactants: A review. Comptes Rendus Chimie. pp. 112-130. Reference may be made to certain commercial examples of amino acid based surfactants, which include AMINAT-G™ from Vedeqsa, and CAE™ from Ajinomoto.

The amount of the at least one cationic surfactant that is an amino acid based cationic surfactant is present in the cleansing composition is in a range of from about 0.01% to about 5%, or from about 0.03% to about 1%, or from about 0.02% to about 2%, or from about 0.05% to about 1% by weight, or from about 0.08% to about 1.5%, or from about 0.1% to about 0.5%, or from about 0.2% to about 0.4%, or any suitable combination, sub-combination, range, or sub-range thereof by weight, based on the weight of the cleansing composition. One of ordinary skill in the art, however, will appreciate that other ranges are within the scope of the invention.

Thus, each of the at least one cationic surfactant in the cleansing composition is present by weight, based on the total weight of the cleansing composition, from about 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, to about 5 percent, by weight, including increments and ranges therein and there between.

Non-Ionic Surfactant

In the various embodiments, the cleansing composition includes in a water phase one or more additional surfactant, in some embodiments, a nonionic surfactant.

Useful alkylpolyglucosides include lauryl glucoside, octyl glucoside, decyl glucoside, coco glucoside, caprylyl/capryl glucoside, sodium lauryl glucose carboxylate, or combinations thereof.

In some representative embodiments the one or more additional surfactant includes at least one nonionic surfactant that includes caprylyl/capryl glucoside.

The amount of the one or more additional surfactant present in the cleansing composition is in a range of from about 0.01% to about 5%, or from about 0.02% to about 2%, or from about 0.05% to about 1% by weight, or from about 0.08% to about 1.5%, or from about 0.1% to about 1.0%, or from about 0.2% to about 0.7%, or any suitable combination, sub-combination, range, or sub-range thereof by weight, based on the weight of the cleansing composition. One of ordinary skill in the art, however, will appreciate that other ranges are within the scope of the invention.

Thus, of the one or more additional surfactant that is present in the cleansing composition is present by weight, based on the total weight of the cleansing composition, from about 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, to about 5 percent, by weight, including increments and ranges therein and there between.

Salt

In the various embodiments, the cleansing composition includes one or more salts, for example, the cleansing composition includes one or more salts selected from the group consisting of sea salt, sodium chloride, magnesium chloride, calcium chloride, potassium chloride, magnesium sulfate, magnesium carbonate, calcium carbonate, and zinc pyrrolidone carboxylic acid, and other suitable mineral salts of sodium, calcium, magnesium, potassium, zinc, and combinations thereof.

In some particular embodiments, the cleansing composition includes sea salt.

And according to such embodiments, the amount of each of the one or more salts, when present, is in a range from about 0.01% to about 5%, or from about 0.02% to about 2%, or from about 0.05% to about 1% by weight, or from about 0.08% to about 1.5%, or from about 0.1% to about 0.5%, or from about 0.1% to about 2%, or from about 0.2% to about 0.4%, or any suitable combination, sub-combination, range, or sub-range thereof by weight, based on the weight of the cleansing composition. One of ordinary skill in the art, however, will appreciate that other ranges are within the scope of the invention.

Thus, any one of the added salts is present, by weight, based on the total weight of the cleansing composition, from about 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, to about 5 percent, by weight, including increments and ranges therein and there between.

Oil

In accordance with the various embodiments, the cleansing composition includes one or more oils. In accordance with some particular embodiments, the cleansing composition includes one or more oils that are natural or nature-based oils. In some particular embodiments, the cleansing composition includes more than two oils, wherein at least one of each of the more than two oils is in a different phase layer of the cleansing composition.

In some particular examples, the cleansing composition includes at least one or more oils present in a phase layer of the cleansing composition wherein the oil comprises at least one plant-derived alkane or plant-derived alkylether. In a representative example of the cleansing composition, at least one phase layer of the cleansing composition includes at least one plant-derived alkylether, and in some particular embodiments, the plant-derived alkylether is dicaprylyl ether.

In some particular examples, the cleansing composition includes at least one or more oils present in a phase layer of the cleansing composition that includes one or more oils that may include an plant-derived alkane or plant-derived alkylether or another oil. In a representative example of the cleansing composition, at least one phase layer of the cleansing composition includes two or more oils selected from the group consisting of a C15-19 alkane, undecane, tridecane, isopropyl palmitate, isododecane, and combinations thereof.

As used herein, oil refers to any nonpolar compound that is a liquid at 25° C. and is hydrophobic and lipophilic. Oil that is suitable for use herein may be volatile or non-volatile. The term "volatile oil" relates to oil that is capable of evaporating on contact with the skin or a keratin fiber in less than one hour, at room temperature and atmospheric pressure. The volatile oil(s) are liquid at room temperature and have a non-zero vapor pressure, at room temperature and atmospheric pressure, ranging in particular from 0.13 Pa to 40 000 Pa (10-3 to 300 mmHg). The term "non-volatile oil" relates to oil which remains on the skin or the keratin fiber, at room temperature and atmospheric pressure, for at least several hours and which in particular has a vapor pressure of less than 10-3 mmHg (0.13 Pa).

In some embodiments, the oils are natural, food-derived oils, and in some particular embodiments, are oils of plant origin. Plant-derived oils include glyceride triesters, which are generally triesters of fatty acids and of glycerol, the fatty acids of which can have varied chain lengths from C4 to C24, it being possible for these chains to be saturated or unsaturated and linear or branched. Reference may be made to certain commercial examples of amino acid based surfactants, which include AMINAT-G™ from Vedeqsa, and CAE™ from Ajinomoto.

Hydrocarbon-Based Oils

The cleansing composition may comprise one or more hydrocarbon-based oils. For example, the hydrocarbon-based oil may be a saturated hydrocarbon, an unsaturated hydrocarbon, lipids, triglycerides, a natural oil, and/or a synthetic oil. In some embodiments, the cleansing composition may include a synthetic oil selected from the group consisting of hydrogenated polyisobutene and hydrogenated polydecene. A hydrocarbon-based oil may be a non-volatile hydrocarbon-based, such as:

(i) hydrocarbon-based oils of plant origin, such as glyceride triesters, which are generally triesters of fatty acids and of glycerol, the fatty acids of which can have varied chain lengths from C4 to C24, it being possible for these chains to be saturated or unsaturated and linear or branched; these oils are in particular wheat germ oil, sunflower oil, grape seed oil, sesame oil, corn oil, apricot oil, castor oil, shea oil, avocado oil, olive oil, soybean oil, sweet almond oil, palm oil, rapeseed oil, cottonseed oil, hazelnut oil, macadamia oil, jojoba oil, alfalfa oil, poppy oil, pumpkin seed oil, marrow oil, blackcurrant oil, evening primrose oil, millet oil, barley oil, *quinoa* oil, rye oil, safflower oil, candlenut oil, passionflower oil, musk rose oil, and essential oils, such as *Helianthus Annuus* Seed Oil, *Lavandula Angustifolia* (lavender) Oil, *Mentha Piperita* Oil, *Rosmarinus Officinalis* (rosemary) Leaf Oil *Pelargonium Graveolens* flower oil, *Citrus Aurantium Dulcis* (orange) peel oil, *Menthe Viridis* (spearmint) leaf oil, *Citrus Aurantifolia* (lime) oil, *Melaleuca Alternifolia* (tea tree) leaf oil, *Citrus Grandis* (grapefruit) peel oil, *Citrus Medica Limonum* (lemon) peel oil, rose flower oil, *eucalyptus globulus* leaf oil, and combinations thereof.

(ii) synthetic ethers containing from 10 to 40 carbon atoms;

(iii) linear or branched hydrocarbons of mineral or synthetic origin, such as petroleum jelly, polydecenes, hydrogenated polyisobutene such as Parleam, and squalane;

(iv) synthetic esters, for instance oils of formula RCOOR' in which R represents a linear or branched fatty acid residue containing from 1 to 40 carbon atoms and R' represents a hydrocarbon-based chain that is especially branched, containing from 1 to 40 carbon atoms on condition that R+R' is ÿ 10, for instance Purcellin oil (cetearyl octanoate), isopropyl myristate, isopropyl palmitate, C12-C15 alkyl benzoate, such as the product sold under the trade name Finsolv TN™ or Witconol TN™ by Witco or Tegosoft TN™ by Evonik Goldschmidt, 2-ethylphenyl benzoate, such as the commercial product sold under the name X-Tend 226 by ISP, isopropyl lanolate, hexyl laurate, diisopropyl adipate, isononyl isononanoate, oleyl erucate, 2-ethylhexyl palmitate, isostearyl isostearate, diisopropyl sebacate, such as the product sold under the name of "Dub Dis" by Stearinerie Dubois, octanoates, decanoates or ricinoleates of alcohols or polyalcohols, such as propylene glycol dioctanoate; hydroxylated esters, such as isostearyl lactate or diisostearyl malate; and pentaerythritol esters; citrates or tartrates, such as di(linear C12-C13 alkyl) tartrates, such as those sold under the name Cosmacol ETI™ by Enichem Augusta Industriale, and also di(linear C14-C15 alkyl) tartrates, such as those sold under the name Cosmacol ETL™ by the same company; or acetates;

(v) fatty alcohols that are liquid at room temperature, containing a branched and/or unsaturated carbon-based chain containing from 12 to 26 carbon atoms, for instance octyldodecanol, isostearyl alcohol, oleyl alcohol, 2-hexyldecanol, 2-butyloctanol or 2-undecylpentadecanol;

(vi) higher fatty acids, such as oleic acid, linoleic acid or linolenic acid;

(vii) carbonates, such as dicaprylyl carbonate, such as the product sold under the name Cetiol CC™ by Cognis;

(viii) fatty amides, such as isopropyl N-lauroyl sarcosinate, such as the product sold under the trade name Eldew SL 205™ from Ajinomoto; and (ix) essential oils selected from the group consisting of sunflower oil, sesame oil, peppermint oil, macadamia nut oil, tea tree oil, evening primrose oil, sage oil, rosemary oil, coriander oil, thyme oil, pimento berries oil, rose oil, anise oil, balsam oil, bergamot oil, rosewood oil, cedar oil, chamomile oil, sage oil, clary sage oil, clove oil, cypress oil, *eucalyptus* oil, fennel oil, sea fennel oil, frankincense oil, geranium oil, ginger oil, grapefruit oil, jasmine oil, juniper oil, lavender oil, lemon oil, lemongrass oil, lime oil, mandarin oil, marjoram oil, myrrh oil, neroli oil, orange oil, patchouli oil, pepper oil, black pepper oil, petitgrain oil, pine oil, rose otto oil, rosemary oil, sandalwood oil, spearmint oil, spikenard oil, vetiver oil, wintergreen oil, and ylang ylang.

In some embodiments, hydrocarbon-based oils may be glyceride triesters and in particular to caprylic/capric acid triglycerides, synthetic esters and in particular isononyl isononanoate, oleyl erucate, C12-C15 alkyl benzoate, 2-ethylphenyl benzoate and fatty alcohols, such as octyldodecanol. As volatile hydrocarbon-based oils, mention is made of hydrocarbon-based oils containing from 8 to 16 carbon atoms and in particular of branched C8-C16 alkanes, such as C8-C16 isoalkanes of petroleum origin (also known as isoparaffins), such as isododecane (also known as 2,2,4,4, 6-pentamethylheptane), isodecane or isohexadecane, the oils sold under the Isopar or Permethyl trade names, branched C C8-C16 esters, and isohexyl neopentanoate.

In some embodiments, the cleansing composition may comprise one or more oils selected from branched or linear, liquid alkane with carbon chain length of C11 to C20. In various embodiments, liquid alkanes may be selected from those with a carbon chain length of from C11 to C20. The liquid alkanes may be selected from those with a carbon chain length of from C11 to C20, or from C15 to C19, or one of C11, C12, C13, C14, C15, C16, C17, C18 to C19. In some particular embodiments, suitable liquid alkanes that may be used according to the disclosure include hydrocarbon-based oils containing from 8 to 16 carbon atoms, and especially branched C8-C16 alkanes such as C8-C16 isoalkanes. In some embodiments, the one or more branched or linear, liquid alkane is selected from the group consisting of C15-19 alkane, undecane, tridecane, isododecane, isohexadecane, and combinations thereof.

In some embodiments the cleansing composition may comprise one or more branched or linear, liquid alkanes. In some embodiments the cosmetic cleansing composition may comprise one or more alkylethers selected from the group consisting of dicaprylyl ether, dicapryl ether, dilauryl ether, diisostearyl ether, dioctyl ether, nonyl phenyl ether, dodecyl dimethylbutyl ether, cetyl dimethylbutyl ether, cetyl isobutyl ether, and combinations thereof.

The amount of each oil present in the cosmetic cleansing composition is in a range of from about 1% to about 50%, or from about 1% to about 25%, or from about 5% to about 20%, or from about 10% to about 15%, or from about 15% to about 20%, or from about 10% to about 40%, or from about 5% to about 50%, or from about 1% to about 12% by weight, or from about 2% to about 10% by weight, or from about 3% to about 5%, or any suitable combination, sub-combination, range, or sub-range thereof by weight, based on the weight of the cosmetic cleansing composition. In some particular embodiments, the oil includes at least one plant-derived alkane or plant-derived alkylether which is present in an amount from about 5% to about 50%, or from about 10% to about 15%, or from about 15% to about 20%, or from about 10% to about 40%. One of ordinary skill in the art, however, will appreciate that other ranges are within the scope of the invention.

Thus, each of the at least one branched or linear, liquid alkane, when present in the cosmetic cleansing composition, may be present by weight, based on the total weight of the cosmetic cleansing composition, from about 1, 2, 3, 4, 5, 6, 7, 8, 9, 10, 11, 12, 13, 14, 15, 16, 17, 18, 19, 20, 21, 22, 23, 24 to about 25 weight percent, including increments and ranges therein and there between.

Humectant

In accordance with the disclosure, one more humectants may be present in the cleansing composition. In some embodiments, the humectant may comprise one or more of polyols, including, for example, glycerin, glycerol, butylene glycol, propylene glycol/propanediol, isoprene glycol, dipropylene glycol, hexylene glycol and polyethylene glycols, monoethylene glycol, diethylene glycol, triethylene glycol, diethylene glycol, hexylene glycol, glycol ethers such as monopropylene, dipropylene and tripropylene glycol alkyl(C1-C4)ethers, squalane, triacetin, sugars, such as glucose, xylitol, maltitol, sorbitol, sucrose pentaerythritol, inositol, pyrrolidone carboxylic acid, lactic acid, lithium chloride, acetamide MEA, sodium lactate, urea, dicyanamide, hyaluronic acid, aloe vera, honey, and seaweed extract.

In some embodiments, the cleansing composition includes the propanediol.

In accordance with the various embodiments, the amount of each humectant, when present in the cleansing composition, can range from about 0.5% to about 10% by weight, or from about 1% to about 10% by weight, or from about 3% to about 8% or any suitable combination, sub-combination, range, or sub-range thereof by weight, based on the weight of the cleansing composition. One of ordinary skill in the art, however, will appreciate that other ranges are within the scope of the invention.

Thus, each of the at least one humectant in the cleansing composition, when present, is present by weight, based on the total weight of the cleansing composition, from about 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5, 6, 7, 8, 9, to about 10 percent, including increments and ranges therein and there between.

Water

In accordance with the various embodiments, water is present in the cleansing composition in a range from about 40% to about 75%, or from about 45% to about 70%, or from about 50% to about 65%, or from about 55%, or from about 60%, or any suitable combination, sub-combination, range, or sub-range thereof by weight, based on the weight of the cleansing composition. One of ordinary skill in the art, however, will appreciate that other ranges are within the scope of the invention. Thus, water is present, by weight, based on the total weight of the cleansing composition, from about 40, 45, 50, 55, 60, 65, 70, 75, to about 80 weight percent, including increments and ranges therein and there between.

The water used may be sterile demineralized water and/or a floral water such as rose water, cornflower water, chamomile water or lime water, and/or a natural thermal or mineral water such as, for example: water from Vittel, water from the Vichy basin, water from Uriage, water from La Roche Posay, water from La Bourboule, water from Enghien-les-bains, water from Saint Gervais-les-Bains, water from Neris-les-Bains, water from Allevar-les-Bains, water from Digne, water from Maizieres, water from Neyrac-les-Bains, water from Lons-le-saunier, water from Eaux Bonnes, water from Rochefort, water from Saint Christau, water from Les Fumades, water from Tercis-les-Bains or water from Avene. The water phase may also comprise reconstituted thermal water, that is to say a water comprising trace elements such as zinc, copper, magnesium, etc., reconstituting the characteristics of a thermal water.

In some embodiments, the pH of the cleansing composition is not limited but is generally between 5 and 9, and in some embodiments, is one of between 6 and 8, and in some embodiments is 7. In some particular embodiments, the pH of the cleansing composition is generally between 4 and 8, and in some embodiments, is one of between 5 and 7, and in some embodiments is 5.5. The pH can be adjusted to the desired value by addition of a base (organic or inorganic) to the cleansing composition, for example ammonia or a primary, secondary or tertiary (poly)amine, such as monoethanolamine, diethanolamine, triethanolamine, isopropanolamine or 1,3-propanediamine, or alternatively by addition of an inorganic or organic acid, advantageously a carboxylic acid, such as, for example, citric acid.

Water-Soluble Solvents

In accordance with some embodiments, the cleansing composition may include at least one water-soluble solvent. The term "water-soluble solvent" is interchangeable with the term "water-miscible solvent" and means a compound that is liquid at 25° C. and at atmospheric pressure (760 mmHg), and it has a solubility of at least 50% in water under these conditions. In some embodiments, the water-soluble solvent has a solubility of at least 60%, 70%, 80%, or 90% in water under these conditions. Non-limiting examples of water-soluble solvents include, for example, glycerin, alcohols (for example, C1-C30, C1-C15, C1-C10, or C1-C4 alcohols), organic solvents, polyols, glycols, or combinations thereof.

In some particular embodiments according to the disclosure, when present, a water-soluble solvent may include caprylyl glycol, glycerin, or combinations thereof.

As examples of organic solvents, non-limiting mentions can be made of monoalcohols and polyols such as ethyl alcohol, isopropyl alcohol, propyl alcohol, benzyl alcohol, and phenylethyl alcohol, or glycols or glycol ethers such as, for example, monomethyl, monoethyl and monobutyl ethers of ethylene glycol, propylene glycol or ethers thereof such as, for example, monomethyl ether of propylene glycol, butylene glycol, hexylene glycol, dipropylene glycol as well as alkyl ethers of diethylene glycol, for example monoethyl ether or monobutyl ether of diethylene glycol. Other suitable examples of organic solvents are ethylene glycol, propylene glycol, butylene glycol, hexylene glycol, propanediol, and glycerin. The organic solvents can be volatile or non-volatile compounds.

Further non-limiting examples of water-soluble solvents include alkanols (polyhydric alcohols such as glycols and polyols) such as glycerin, 1,2,6-hexanetriol, trimethylolpropane, ethylene glycol, propylene glycol, diethylene glycol, butylene glycol, hexylene glycol, triethylene glycol, tetraethylene glycol, pentaethylene glycol, dipropylene glycol, 1,3-butanediol, 2,3-butanediol, 1,4-butanediol, 3-methyl-1,3-butanediol, 1,5-pentanediol, tetraethylene glycol, 1,6-hexanediol, 2-methyl-2,4-pentanediol, polyethylene glycol, 1,2,4-butanetriol, 1,2,6-hexanetriol, 2-butene-1,4-diol, 2-ethyl-1,3-hexanediol, 2-methyl-2,4-pentanediol, (caprylyl glycol), 1,2-hexanediol, 1,2-pentanediol, and 4-methyl-1,2-pentanediol; alkyl alcohols having 1 to 4 carbon atoms such as ethanol, methanol, butanol, propanol, and isopropanol; glycol ethers such as ethylene glycol monomethyl ether, ethylene glycol monoethyl ether, ethylene glycol monobutyl ether, ethylene glycol monomethyl ether acetate, diethylene glycol monomethyl ether, diethylene glycol monoethyl ether, diethylene glycol mono-n-propyl ether, ethylene glycol mono-iso-propyl ether, diethylene glycol mono-iso-propyl ether, ethylene glycol mono-n-butyl ether, ethylene glycol mono-t-butyl ether, diethylene glycol mono-t-butyl ether, 1-methyl-1-methoxybutanol, propylene glycol monomethyl ether, propylene glycol monoethyl ether, propylene glycol mono-t-butyl ether, propylene glycol mono-n-propyl ether, propylene glycol mono-iso-propyl ether, dipropylene glycol monomethyl ether, dipropylene glycol monoethyl ether, dipropylene glycol mono-n-propyl ether, and dipropylene glycol mono-iso-propyl ether; 2-pyrrolidone, N-methyl-2-pyrrolidone, 1,3-dimethyl-2-imidazolidinone, formamide, acetamide, dimethyl sulfoxide, sorbit, sorbitan, acetine, diacetine, triacetine, sulfolane, or combinations thereof.

In some embodiments, a water-soluble solvent may be propanediol or glycerin.

In accordance with the various embodiments the amount of the at least one water-soluble solvent, when present, is from about 0.1% to about 10%, or from about 1% to about 10%, or from about 2% to about 8%, or any suitable combination, sub-combination, range, or sub-range thereof by weight, based on the weight of the cleansing composition. One of ordinary skill in the art, however, will appreciate that other ranges are within the scope of the invention. In some embodiments, the cleansing composition includes more than one water soluble solvent, each water soluble solvent present in an amount as set forth herein above, wherein each different water soluble solvent may be present within one of the ranges selected from the ranges set forth herein above.

Thus, each one or combination of water-soluble solvents, when present, may be present by weight, based on the total weight of the cleansing composition, from about 0.1, 0.2, 0.3, 0.4, 0.5, 0.6, 0.7, 0.8, 0.9, 1, 2, 3, 4, 5, 6, 7, 8, 9, to about 10 weight percent, including increments and ranges therein and there between.

Preservatives

In accordance with the disclosure, one or more preservatives may be present in the cleansing composition. In some embodiments, the one or more preservatives, when present, may be selected from Myrtrimonium bromide, phenoxyethanol, hydroxyacetophenone, ethylhexyl glycerin, chlorphenesin, cetrimonium chloride, caprylyl glycol, hexyl glycerin, octylglycerin, benzylglycerin, 3-heptoyl-2,2-propandiol, and 1,2-hexandiol; polyaminopropyl biguanide, also known as polyhexamethylene biguanide, or PHMB, and combinations thereof. In some embodiments, the cleansing composition is free or essentially free of one or more of caprylyl glycol, phenoxyethanol, hexyl glycerin, ethylhexylglycerin, octylglycerin, benzylglycerin, 3-heptoyl-2,2-propandiol, and 1,2-hexandiol; polyaminopropyl biguanide, also known as polyhexamethylene biguanide, or PHMB.

In some embodiments, the one more preservatives includes Myrtrimonium bromide, phenoxyethanol, hydroxyacetophenone, and combinations thereof.

In accordance with the various embodiments, the amount of each one of the one more preservatives if present in the cleansing composition can range from about 0.01% to about 1% by weight, or from about 0.02% to about 0.5% by weight, or from about 0.03% to about 0.1% or any suitable combination, sub-combination, range, or sub-range thereof by weight, based on the weight of the cleansing composition. One of ordinary skill in the art, however, will appreciate that other ranges are within the scope of the invention.

Thus, each one of the one more preservatives, when present in the cleansing composition, is present by weight, based on the total weight of the cleansing composition, from about 0.01, 0.02, 0.03, 0.04, 0.05, 0.06, 0.07, 0.08, 0.09, 0.10, 0.20, 0.30, 0.40, 0.50, 0.60, 0.70, 0.80, 0.90, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9 to about 3 weight percent, including increments and ranges therein and there between.

Additives

The cleansing composition can also comprise at least one additive used in the cosmetics field which does not affect the properties of the cleansing composition according to the invention, such as additives selected from fragrances, vitamins, colorants; essential oils; fruit extracts, for example *Pyrus Malus* (Apple) Fruit Extract, and *Aloe Barbadensis* Leaf Juice Powder; citric acid, sodium chloride; neutralizing or pH-adjusting agents (e.g., triethylamine (TEA) and sodium hydroxide); and combinations thereof.

Although the optional active additives are given as examples, it will be appreciated that other optional components compatible with cosmetic applications known in the art may be used. Although the optional additives are given as examples, it will be appreciated that other optional components compatible with cosmetic applications known in the art may be used.

In accordance with the various embodiments, the amount of one or more actives and additives, alone or in combination, present in the cleansing composition can be present in the cleansing composition according to the disclosure in a range from about 0.001% to about 20%, by weight, or from about 0.005% to about 0.01%, or from about 0.01% to about 0.1%, or from about 0.15% to about 5%, or from about 0.40% to about 4%, or from about 0.5% to about 2.5% by weight, or from about 1% to about 2%, or any suitable combination, sub-combination, range, or sub-range thereof by weight, based on the total weight of the cleansing composition.

Thus, any one or a combination of actives and additives may be present, by weight, based on the total weight of the cleansing composition, each one or the combination present from about 0.001, 0.002, 0.003, 0.004, 0.005, 0.006, 0.007, 0.008, 0.009, 0.01, 0.02, 0.03, 0.04, 0.05, 0.06, 0.07, 0.08, 0.09, 0.10, 0.20, 0.30, 0.40, 0.50, 0.60, 0.70, 0.80, 0.90, 1.0, 2, 3, 4, 5, 6, 7, 8, 9, 10, 11, 12, 13, 14, 15, 16, 17, 18, 19 to about 20 weight percent, including increments and ranges therein and there between.

EXAMPLES

Example 1: Inventive Compositions

One example of this multiphase cleansing composition is disclosed in the Formula 1 (see Table 1). When left standing, Formula 1 forms three visibly distinct layers. When agitated, the cleansing composition forms a milky single phase. For Formula 1, pH was adjusted to pH 5.3±0.4 by using Glutamic acid and Sodium Hydroxide.

TABLE 1

Inventive Formula 1: a 2-phase cosmetic liquid composition

| Phase | wt % | INCI |
|---|---|---|
| Top Phase | 20% | DICAPRYLYL ETHER |
| Bottom Phase | 53.45% | WATER |
| | 0.5% | CAPRYLYL/CAPRYL GLUCOSIDE |
| | 0.50% | GLYCERIN AND ETHYL LAUROYL ARGINATE HCL |
| | 5% | PROPANEDIOL |
| | 0.8% | SODIUM CHLORIDE |

*All amounts are final concentration of active; Glycerin Ethyl Lauroyl Arginate Raw Material has active present from about 50% to about 100%.

Another example of this multiphase cleansing composition is disclosed in the Formula 2 (see Table 2). When left standing, Formula 2 forms three visibly distinct layers. When agitated, the cleansing composition forms a milky single phase. For Formula 2, pH was adjusted to pH 5.3±0.4 by using Glutamic acid and Sodium Hydroxide.

TABLE 2

Inventive Formula 2: a 2-phase cosmetic liquid composition

| Phase | wt % | INCI |
|---|---|---|
| Bottom Phase (water phase) | 74.54% | Water |
| | 0.1% | PCA Ethyl Cocoyl Arginate |
| | 4.00% | PROPANEDIOL |
| | 0.10% | Caprylyl Glycol |
| | 0.20% | Poltyglyceryl-4 Caprate |
| | 0.06% | Glutamic acid |
| | 1% | Sodium Chloride |
| Top Phase | 12% | Undecaneand Tridecane |
| | 8% | C15-19 Alkane |

*All amounts are final concentration of active; PCA Ethyl Cocoyl Arginate Raw Material has active present from about 50% to about 100%.

Another example of this multiphase cleansing composition is disclosed in the Formula 3 (see Table 3). When left standing, Formula 3 forms three visibly distinct layers. When agitated, the cleansing composition forms a milky single phase. For Formula 3, pH was adjusted to pH 5.3±0.4 by using Glutamic acid and Sodium Hydroxide.

TABLE 3

Inventive Formula 3: a 2-phase cosmetic liquid composition

| Phase | wt % | INCI |
|---|---|---|
| Bottom Phase (water phase) | 55.92% | Water |
| | 0.06% | PCA Ethyl Cocoyl Arginate |
| | 3.00% | PROPANEDIOL |
| | 0.075% | Caprylyl Glycol |
| | 0.15% | Poltyglyceryl-4 Caprate |
| | 0.045% | Glutamic acid |
| | 0.75% | Sodium Chloride |
| Top Phase | 24% | Undecaneand Tridecane |
| | 16% | C15-19 Alkane |

*All amounts are final concentration of active; PCA Ethyl Cocoyl Arginate Raw Material has active present from about 50% to about 100%.

Another example of this multiphase cleansing composition is disclosed in the Formula 4 (see Table 4). When left standing, Formula 4 forms three visibly distinct layers. When agitated, the cleansing composition forms a milky single phase. For Formula 4, pH was adjusted to pH 5.3±0.4 by using Glutamic acid and Sodium Hydroxide.

TABLE 4

Inventive Formula 4: a 2-phase cosmetic liquid composition

| Phase | wt % | INCI |
|---|---|---|
| Bottom Phase (water phase) | 74.56% | Water |
| | 0.08% | PCA Ethyl Cocoyl Arginate |
| | 4.00% | PROPANEDIOL |
| | 0.10% | Caprylyl Glycol |
| | 0.20% | Poltyglyceryl-4 Caprate |
| | 0.06% | Glutamic acid |
| | 1% | Sodium Chloride |
| Top Phase | 12% | Isododecane |
| | 8% | Isohexadecane |

*All amounts are final concentration of active; PCA Ethyl Cocoyl Arginate Raw Material has active present from about 50% to about 100%.

Another example of this multiphase cleansing composition is disclosed in the Formula 5 (see Table 5). When left standing, Formula 5 forms three visibly distinct layers. When agitated, the cleansing composition forms a milky single phase. For Formula 5, pH was adjusted to pH 5.3±0.4 by using Glutamic acid and Sodium Hydroxide.

TABLE 5

Inventive Formula 5: a 2-phase cosmetic liquid composition

| Phase | wt % | INCI |
|---|---|---|
| Bottom Phase (water phase) | 74.54% | Water |
| | 0.1% | PCA Ethyl Cocoyl Arginate |
| | 4.00% | PROPANEDIOL |
| | 0.10% | Caprylyl Glycol |
| | 0.20% | Poltyglyceryl-4 Caprate |
| | 0.06% | Glutamic acid |
| | 1% | Sodium Chloride |
| Top Phase | 12% | Isododecane |
| | 8% | Isohexadecane |

*All amounts are final concentration of active; PCA Ethyl Cocoyl Arginate Raw Material has active present from about 50% to about 100%.

Another example of this multiphase cleansing composition is disclosed in the Formula 2 (see Table 2). When left standing, Formula 2 forms three visibly distinct layers. When agitated, the cleansing composition forms a milky single phase. For Formula 2, pH was adjusted to pH 5.3±0.4 by using Glutamic acid and Sodium Hydroxide.

Example 2: Comparative Compositions

TABLE 6

Comparative Formula BF: a 2-phase cosmetic liquid composition

| | wt % | Composition |
|---|---|---|
| Top Phase | 38.5% | Oil Phase of Bi-Facil |
| Bottom Phase | 61.5% | Water Phase of Bi-Facil |

TABLE 7

Comparative Formula BPAN: a 2-phase cosmetic liquid composition

| | wt % | INCI |
|---|---|---|
| Top Phase | 19.2% | C15-19 ALKANE |
| | 19.2% | Undecane and Tridecane |
| Bottom Phase | 0.31% | Sea Salt |
| | 0.31% | PCA Ethyl Cocoyl Arginate |
| | 60.9% | Water |

Example 3: Evaluation of Makeup Removal with Inventive Composition Vs Commercial Benchmark Comparative Compositions We unexpectedly discovered that this type of multiphase cosmetic liquid compositions may enhance makeup removal performance with a broader spectrum for different types of makeup films.

Inventive and Comparative compositions were tested in a study in which foundation were applied to skin and dried for 30 min. Each of the multiphase liquid compositions including Formula 1, Formula BF, and Formula BPAN was agitated and 1 gram of the formed single phase mixture was transferred to a cotton pad. Each of the wetted cotton pads were rubbed six times against the makeup film on skin, and the makeup removability was assessed after rubbing. The results demonstrate that Formula 1 showed a comparable removal performance as the comparative Formula BPAN, and better than comparative Formula BF.

Inventive and Comparative compositions were tested in a study in which Mascara was evenly spread on skin and subsequently dried for 1 hour. Each of the multiphase liquid compositions including Formula 1 and Formula BF was agitated and 1 gram of the formed single phase mixture was transferred to a cotton pad. Each of the wetted cotton pads were rubbed two times against the mascara film on skin, and the removability was assessed after rubbing. The results demonstrate that Formula 1 showed better removal performance than comparative Formula BF.

Raw Materials:

Undecane and Tridecane; Caprylyl/Capryl Glucoside, ~60% purity; Ethyl Lauroyl Arginate HCl and Glycerin), between 50% to 100% purity of active; PCA Ethyl Cocoyl Arginate, between 50% to 100% purity.

While the disclosure has been described with reference to a preferred embodiment, it will be understood by those skilled in the art that various changes may be made and equivalents may be substituted for elements thereof without departing from the scope of the disclosure. In addition, many modifications may be made to adapt a particular situation or material to the teachings of the disclosure without departing from the essential scope thereof. While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

The articles "a" and "an," as used herein, mean one or more when applied to any feature in embodiments of the present disclosure described in the specification and claims. The use of "a" and "an" does not limit the meaning to a single feature unless such a limit is specifically stated. The article "the" preceding singular or plural nouns or noun phrases denotes a particular specified feature or particular specified features and may have a singular or plural connotation depending upon the context in which it is used. The adjective "any" means one, some, or all indiscriminately of whatever quantity.

"At least one," as used herein, means one or more and thus includes individual components as well as mixtures/combinations.

The transitional terms "comprising," "consisting essentially of" and "consisting of", when used in the appended claims, in original and amended form, define the claim scope with respect to what unrecited additional claim elements or steps, if any, are excluded from the scope of the claim(s). The term "comprising" is intended to be inclusive or open-ended and does not exclude any additional, unrecited element, method, step or material. The term "consisting of" excludes any element, step or material other than those specified in the claim and, in the latter instance, impurities ordinarily associated with the specified material(s). The term "consisting essentially of" limits the scope of a claim to the specified elements, steps or material(s) and those that do not materially affect the basic and novel characteristic(s) of the claimed disclosure. All materials and methods described herein that embody the present disclosure can, in alternate embodiments, be more specifically defined by any of the transitional terms "comprising," "consisting essentially of," and "consisting of."

The terms "free" and "devoid" and "excludes" indicates that no reliably measurable excluded material is present in the cleansing composition, typically 0% by weight, based on the total weight of the cleansing composition. The term "essentially free" means that, while it prefers that no excluded material is present in the cleansing composition, it is possible to have very small amounts of the excluded material in the cleansing composition of the invention, provided that these amounts do not materially affect the advantageous properties of the cleansing composition. In particular, "essentially free" means that excluded material can be present in the cleansing composition at an amount of less than about 0.1% by weight, based on the total weight of the cleansing composition.

All percentages and ratios are calculated by weight unless otherwise indicated. All percentages are calculated based on the total composition unless otherwise indicated. Generally, unless otherwise expressly stated herein, "weight" or "amount" as used herein with respect to the percent amount of an ingredient refers to the amount of the raw material comprising the ingredient, wherein the raw material may be described herein to comprise less than and up to 100% activity of the ingredient. Therefore, weight percent of an active in a composition is represented as the amount of raw material containing the active that is used and may or may not reflect the final percentage of the active, wherein the final percentage of the active is dependent on the weight percent of active in the raw material.

All ranges and amounts given herein are intended to include subranges and amounts using any disclosed point as an end point. Thus, a range of "1% to 10%, such as 2% to 8%, such as 3% to 5%," is intended to encompass ranges of "1% to 8%," "1% to 5%," "2% to 10%," and so on. All numbers, amounts, ranges, etc., are intended to be modified by the term "about," whether or not so expressly stated. Similarly, a range given of "about 1% to 10%" is intended to have the term "about" modifying both the 1% and the 10% endpoints. Further, it is understood that when an amount of a component is given, it is intended to signify the amount of the active material unless otherwise specifically stated.

Notwithstanding that the numerical ranges and parameters setting forth the broad scope of the disclosure are approximations, unless otherwise indicated the numerical values set forth in the specific examples are reported as precisely as possible. Any numerical value, however, inherently contains certain errors necessarily resulting from the standard deviation found in their respective testing measurements. The examples serve to illustrate embodiments of the present disclosure without, however, being limiting in nature.

All publications and patent applications cited in this specification are herein incorporated by reference, and for any and all purposes, as if each individual publication or patent application were specifically and individually indicated to be incorporated by reference. In the event of an inconsistency between the present disclosure and any publications or patent application incorporated herein by reference, the present disclosure controls.

The invention claimed is:

1. A cleansing composition, consisting of:
    a first visually distinct phase layer having:
        at least one amino-acid derived cationic surfactant; and
        at least one inorganic salt;
    a second visually distinct phase layer having:
        at least one plant-derived alkane or plant-derived alkylether; and
    optionally, at least one additional visually distinct phase layer,
    the cleansing composition optionally having, in any one or more of the first visually distinct phase layer, the second visually distinct phase layer, and, if present, the at least one additional visually distinct phase layer, at least one additional ingredient,
    wherein the at least one additional ingredient is selected from the group consisting of:
        at least one glycol ether selected from the group consisting of diethylene glycol, diethylene glycol monoethyl ether, diethylene glycol mono-iso-propyl ether, diethylene glycol monomethyl ether, diethylene glycol mono-n-propyl ether, diethylene glycol mono-t-butyl ether, dipropylene glycol, dipropylene glycol monoethyl ether, dipropylene glycol mono-iso-propyl ether, dipropylene glycol monomethyl ether, dipropylene glycol mono-n-propyl ether, ethylene glycol monoethyl ether, ethylene glycol mono-iso-propyl ether, ethylene glycol mono-n-butyl ether, ethylene glycol mono-t-butyl ether, monobutyl ethers of diethylene glycol, monobutyl ethers of ethylene glycol, monoethyl ethers of ethylene glycol, monoethyl ethers of diethylene glycol, monomethyl ether, monomethyl ether acetate, monomethyl ether of butylene glycol, monomethyl ether of dipropylene glycol, monomethyl ether of hexylene glycol, monomethyl ether of propylene glycol, monomethyl ethers of ethylene glycol, pentaethylene glycol, polyethylene glycol, polyethylene glycols, polyglyceryl-4 caprate, propylene glycol monoethyl ether, propylene glycol mono-iso-propyl ether, propylene glycol monomethyl ether, propylene glycol mono-n-propyl ether, propylene glycol mono-t-butyl ether, tetraethylene glycol, triethylene glycol, tripropylene glycol, monopropylene, dipropylene and tripropylene glycol alkyl(C1-C4)ethers, and combinations thereof;
        at least one liquid alkane selected from the group consisting of C8-C20 alkanes and combinations thereof;
        at least one hydroxylated ester selected from the group consisting of isostearyl lactate, diisostearyl malate, and combinations thereof;
        at least one glycerol ester selected from the group consisting of acetine, diacetine, triacetine, and combinations thereof;
        at least one nonionic surfactant;
        at least one cosmetically acceptable solvent,
        at least one oil selected from the group consisting of wheat germ oil, sunflower oil, grape seed oil, sesame oil, corn oil, apricot oil, castor oil, shea oil, avocado oil, olive oil, soybean oil, sweet almond oil, palm oil, rapeseed oil, cottonseed oil, hazelnut oil, macadamia oil, jojoba oil, alfalfa oil, poppy oil, pumpkin seed oil, marrow oil, blackcurrant oil, evening primrose oil, millet oil, barley oil, *quinoa* oil, rye oil, safflower oil, candlenut oil, passionflower oil, musk rose oil, essential oils, *Helianthus annuus* seed oil, *Lavandula angustifolia* oil, *Mentha piperita* oil, *Rosmarinus officinalis* leaf oil *Pelargonium graveolens* flower oil, *Citrus aurantium dulcis* peel oil, *Menthe viridis* leaf oil, *Citrus aurantifolia* oil, *Melaleuca alternifolia* leaf oil, *Citrus grandis* peel oil, *Citrus medica* limonum peel oil, rose flower oil, *eucalyptus globulus* leaf oil, petroleum jelly, polydecenes, hydrogenated polyisobutenen parleam, squalane, purcellin oil, isopropyl myristate, isopropyl palmitate, C12-C15 alkyl benzoate, 2-ethylphenyl benzoate, isopropyl lanolate, hexyl laurate, diisopropyl adipate, isononyl isononanoate, oleyl erucate, 2-ethylhexyl palmitate, isostearyl isostearate, diisopropyl sebacate, octanoates, decanoates or ricinoleates of alcohols or polyalcohols, propylene glycol dioctanoate, pentaerythritol esters, citrates or tartrates, di(linear C12-C13 alkyl) tartrates, di(linear C14-C15 alkyl) tartrates, fatty alcohols that are liquid at room temperature having a branched and/or unsaturated carbon-based chain containing from 12 to 26 carbon atoms, octyldodecanol, isostearyl alcohol, oleyl alcohol, 2-hexyldecanol, 2-butyloctanol, 2-undecylpentadecanol, oleic acid, linoleic acid, linolenic acid, carbonates, dicaprylyl carbonate, fatty amides, isopropyl N-lauroyl sarcosinate, and combinations thereof;
        at least one polyol;
        at least one humectant selected from the group consisting of sugar, glucose, xylitol, maltitol, sorbitol, sucrose pentaerythritol, inositol, pyrrolidone carboxylic acid, lactic acid, lithium chloride, acetamide MEA, sodium lactate, urea, dicyanamide, hyaluronic acid, aloe vera, honey, seaweed extract, and combinations thereof;
        at least one preservative;
        at least one fragrance;

at least one vitamin;
at least one colorants;
at least one fruit extract;
citric acid;
sodium chloride;
glutamic acid;
at least one neutralizing agent;
at least one pH-adjusting agent; and
combinations thereof, and
wherein the cleansing composition is free of each of hexyl glycerin, ethylhexylglycerin, octylglycerin, and benzylglycerin.

2. The cleansing composition according to claim 1, wherein the at least one amino acid derived cationic surfactant is selected from the group consisting of a derivative of ethyl lauroyl arginate or a salt thereof, ethyl cocoyl arginate or a salt thereof, and a combination thereof.

3. The cleansing composition according to claim 1, wherein the at least one inorganic salt is selected from the group consisting of sea salt, sodium chloride, magnesium chloride, calcium chloride, potassium chloride, magnesium sulfate, magnesium carbonate, calcium carbonate, and zinc pyrrolidone carboxylic acid, and other suitable mineral salts of sodium, calcium, magnesium, potassium, zinc, and combinations thereof.

4. The cleansing composition according to claim 1, wherein the at least one plant-derived alkane or plant-derived alkylether in the second visually distinct phase layer comprises an alkylether selected from the group consisting of dicaprylyl ether, dicapryl ether, dilauryl ether, diisostearyl ether, dioctyl ether, nonyl phenyl ether, dodecyl dimethylbutyl ether, cetyl dimethylbutyl ether, cetyl isobutyl ether, and combinations thereof.

5. The cleansing composition according to claim 1, wherein the first visually distinct phase layer comprises the at least one cationic surfactant present in the cleansing composition from about 0.03% to about 1%, by weight, based on the total weight of the cleansing composition.

6. The cleansing composition according to claim 1, wherein the first visually distinct phase layer comprises the at least one inorganic salt present in the cleansing composition from about 0.1% to about 2%, by weight, based on the total weight of the cleansing composition.

7. The cleansing composition according to claim 1, wherein the first visually distinct phase layer is present in the cleansing composition at about 50% to about 95%, and wherein the second visually distinct phase layer is present in the cleansing composition at about 5% to about 50%, all amounts by weight, based on the total weight of the cleansing composition.

8. The cleansing composition according to claim 1, wherein the cleansing composition, when agitated, forms a milky single phase which separates after agitation into three or more visibly distinct phases in a maximum period of 24 hours, and wherein the cleansing composition demonstrates essentially no clinging or dragging of a layer on a container wall and there are no or minimal liquid droplets visible at any phase interface.

9. The cleansing composition according to claim 1, wherein the at least one nonionic surfactant is present in the cleansing composition.

10. The cleansing composition according to claim 1, wherein the at least one cosmetically acceptable solvent, being selected from the group consisting of water, water based solvents, and combinations thereof, is present in the first visually distinct phase layer.

11. The cleansing composition according to claim 1, wherein, the at least one cosmetically acceptable solvent, having water and one or more of glycerin or propanediol, is present in the first visually distinct phase layer.

12. The cleansing composition according to claim 1, wherein the cleansing composition has at least a top and a bottom layer, and wherein the visually distinct phase layer having at least one plant-derived alkane or plant-derived alkylether is the top layer, and the visually distinct phase layer having at least one amino-acid derived cationic surfactant and at least one inorganic salt is the bottom layer.

13. The cleansing composition according to claim 1, wherein the at least one additional visually distinct phase layer is present in the cleansing composition.

14. The cleansing composition according to claim 1, wherein the at least one additional visually distinct phase layer is present in the cleansing composition and wherein the at least one additional visually distinct phase layer is selected from the group consisting of (i) a visually distinct phase layer comprising at least one cosmetic solvent having a Hildebrand solubility parameter δ value that is greater than 15 $cal^{1/2}$ $cm^{-3/2}$ and comprising at least one cationic surfactant and at least one inorganic salt; (ii) a visually distinct phase layer comprising at least one cosmetic solvent having a Hildebrand solubility parameter δ value less than 7.5 $cal^{1/2}$ $cm^{-3/2}$; (iii) a visually distinct phase layer comprising at least one cosmetic solvent having a Hildebrand solubility parameter δ value that is between 8 and 10 $cal^{1/2}$ $cm^{-3/2}$; and combinations thereof.

15. The cleansing composition according to claim 1, wherein the at least one additional visually distinct phase layer is present in the cleansing composition and the at least one additional visually distinct phase layer has at least one cosmetic solvent having a Hildebrand solubility parameter δ value that is less than 7.5 $cal^{1/2}$ $cm^{-3/2}$ or that is between 8 and 10 $cal^{1/2}$ $cm^{-3/2}$.

16. The cleansing composition according to claim 15, wherein the at least one additional visually distinct phase layer is present in the cleansing composition and the at least one additional visually distinct phase layer has isododecane.

17. A cleansing composition, consisting of:
a first visually distinct phase layer having:
at least one amino-acid derived cationic surfactant selected from the group consisting of a derivative of ethyl lauroyl arginate or a salt thereof and ethyl cocoyl arginate or a salt thereof; and
at least one inorganic salt selected from the group consisting of sea salt, sodium chloride, magnesium chloride, calcium chloride, potassium chloride, magnesium sulfate, magnesium carbonate, calcium carbonate, and zinc pyrrolidone carboxylic acid, and other suitable mineral salts of sodium, calcium, magnesium, potassium, zinc, and combinations thereof; and
at least one nonionic surfactant selected from the group consisting of lauryl glucoside, octyl glucoside, decyl glucoside, coco glucoside, caprylyl/capryl glucoside, sodium lauryl glucose carboxylate, and combinations thereof;
a second visually distinct phase layer having at least one plant-derived alkylether selected from the group consisting of dicaprylyl ether, dicapryl ether, dilauryl ether, diisostearyl ether, dioctyl ether, nonyl phenyl ether, dodecyl dimethylbutyl ether, cetyl dimethylbutyl ether, cetyl isobutyl ether, and combinations thereof; and
optionally, at least one additional visually distinct phase layer, the cleansing composition optionally having, in any one or more of the first visually distinct phase layer, the second visually distinct phase layer, and, if present, the at least one additional visually distinct phase layer has at least one additional ingredient, wherein the at least one additional ingredient is selected from the group consisting of:

at least one glycol ether selected from the group consisting of diethylene glycol, diethylene glycol monoethyl ether, diethylene glycol mono-iso-propyl ether, diethylene glycol monomethyl ether, diethylene glycol mono-n-propyl ether, diethylene glycol mono-t-butyl ether, dipropylene glycol, dipropylene glycol monoethyl ether, dipropylene glycol mono-iso-propyl ether, dipropylene glycol monomethyl ether, dipropylene glycol mono-n-propyl ether, ethylene glycol monoethyl ether, ethylene glycol mono-iso-propyl ether, ethylene glycol mono-n-butyl ether, ethylene glycol mono-t-butyl ether, monobutyl ethers of diethylene glycol, monobutyl ethers of ethylene glycol, monoethyl ethers of ethylene glycol, monoethyl ethers of diethylene glycol, monomethyl ether, monomethyl ether acetate, monomethyl ether of butylene glycol, monomethyl ether of dipropylene glycol, monomethyl ether of hexylene glycol, monomethyl ether of propylene glycol, monomethyl ethers of ethylene glycol, pentaethylene glycol, polyethylene glycol, polyethylene glycols, polyglyceryl-4 caprate, propylene glycol monoethyl ether, propylene glycol mono-iso-propyl ether, propylene glycol monomethyl ether, propylene glycol mono-n-propyl ether, propylene glycol mono-t-butyl ether, tetraethylene glycol, triethylene glycol, tripropylene glycol, monopropylene, dipropylene and tripropylene glycol alkyl(C1-C4)ethers, and combinations thereof;

at least one liquid alkane selected from the group consisting of C8-C20 alkanes and combinations thereof;

at least one hydroxylated ester selected from the group consisting of isostearyl lactate, diisostearyl malate, and combinations thereof;

at least one glycerol esters selected from the group consisting of acetine, diacetine, triacetine, and combinations thereof;

at least one additional nonionic surfactant;

at least one cosmetically acceptable solvent, at least one oil selected from the group consisting of wheat germ oil, sunflower oil, grape seed oil, sesame oil, corn oil, apricot oil, castor oil, shea oil, avocado oil, olive oil, soybean oil, sweet almond oil, palm oil, rapeseed oil, cottonseed oil, hazelnut oil, macadamia oil, jojoba oil, alfalfa oil, poppy oil, pumpkin seed oil, marrow oil, blackcurrant oil, evening primrose oil, millet oil, barley oil, *quinoa* oil, rye oil, safflower oil, candlenut oil, passionflower oil, musk rose oil, essential oils, *Helianthus annuus* seed oil, *Lavandula angustifolia* oil, *Mentha piperita* oil, *Rosmarinus officinalis* leaf oil *Pelargonium graveolens* flower oil, *Citrus aurantium dulcis* peel oil, *Menthe viridis* leaf oil, *Citrus aurantifolia* oil, *Melaleuca alternifolia* leaf oil, *Citrus grandis* peel oil, *Citrus medica limonum* peel oil, rose flower oil, *eucalyptus globulus* leaf oil, petroleum jelly, polydecenes, hydrogenated polyisobutenen parleam, squalane, purcellin oil, isopropyl myristate, isopropyl palmitate, C12-C15 alkyl benzoate, 2-ethylphenyl benzoate, isopropyl lanolate, hexyl laurate, diisopropyl adipate, isononyl isononanoate, oleyl erucate, 2-ethylhexyl palmitate, isostearyl isostearate, diisopropyl sebacate, octanoates, decanoates or ricinoleates of alcohols or polyalcohols, propylene glycol dioctanoate, pentaerythritol esters, citrates or tartrates, di(linear C12-C13 alkyl) tartrates, di(linear C14-C15 alkyl) tartrates, fatty alcohols that are liquid at room temperature having a branched and/or unsaturated carbon-based chain containing from 12 to 26 carbon atoms, octyldodecanol, isostearyl alcohol, oleyl alcohol, 2-hexyldecanol, 2-butyloctanol, 2-undecylpentadecanol, oleic acid, linoleic acid, linolenic acid, carbonates, dicaprylyl carbonate, fatty amides, isopropyl N-lauroyl sarcosinate, and combinations thereof;

at least one polyol;

at least one humectant selected from the group consisting of sugar, glucose, xylitol, maltitol, sorbitol, sucrose pentaerythritol, inositol, pyrrolidone carboxylic acid, lactic acid, lithium chloride, acetamide MEA, sodium lactate, urea, dicyanamide, hyaluronic acid, aloe vera, honey, seaweed extract, and combinations thereof;

at least one preservative;

at least one fragrance;

at least one vitamin;

at least one colorants;

at least one fruit extract;

citric acid;

sodium chloride;

glutamic acid;

at least one neutralizing agent;

at least one pH-adjusting agent; and combinations thereof, and wherein the cleansing composition is free of each of hexyl glycerin, ethylhexylglycerin, octylglycerin, and benzylglycerin.

18. The cleansing composition according to claim 1, wherein the first visually distinct phase layer comprises the at least one cationic surfactant present in the cleansing composition from about 0.03% to about 1% and comprises the at least one inorganic salt present in the cleansing composition from about 0.1% to about 2%, and wherein the second visually distinct phase layer comprises at least one plant-derived alkylether present in the cleansing composition at about 5% to about 50%, all amounts by weight, based on the total weight of the cleansing composition.

19. A method for forming the cleansing composition of claim 1, the method comprising:

(a) forming the first visually distinct phase layer;

(b) forming the second visually distinct phase layer; and (c) combining the first visually distinct phase layer and the second the second visually distinct phase layers to provide the cleansing composition wherein each of the phase layers are visually distinct, and wherein, when agitated, the cleansing composition forms a milky single phase which separates after agitation into two or more visibly distinct phases in a maximum period of 24 hours.

20. The method for forming the cleansing composition according to claim 19, wherein:

(a) in the first visually distinctive phase layer, the at least one amino acid derived cationic surfactant is selected from the group consisting of a derivative of ethyl lauroyl arginate or a salt thereof, and ethyl cocoyl arginate or a salt thereof, the at least on nonionic surfactant, if present, is selected from the group consisting of lauryl glucoside, octyl glucoside, decyl glucoside, coco glucoside, caprylyl/capryl glucoside, sodium lauryl glucose carboxylate, and combinations thereof; the at least one inorganic salt selected from the group consisting of sea salt, sodium chloride, magnesium chloride, calcium chloride, potassium chloride, magnesium sulfate, magnesium carbonate, calcium carbonate, and zinc pyrrolidone carboxylic acid, and other suitable mineral salts of sodium, calcium, magnesium, potassium, zinc, and combinations thereof;

(b) in the second visually distinctive phase layer, the at least one plant-derived alkane or alkylether has at least an alkylether selected from the group consisting of dicaprylyl ether, dicapryl ether, dilauryl ether, diisostearyl ether, dioctyl ether, nonyl phenyl ether, dodecyl dimethylbutyl ether, cetyl dimethylbutyl ether, cetyl isobutyl ether, and combinations thereof, wherein the cleansing composition has at least a top and a bottom layer, and wherein the first visually distinctive phase layer is the bottom layer, and the second visually distinctive phase layer is the top layer.

\* \* \* \* \*